United States Patent [19]
Mehra

[11] Patent Number: 5,342,414
[45] Date of Patent: Aug. 30, 1994

[54] TRANSVENOUS DEFIBRILLATION LEAD

[75] Inventor: Rahul Mehra, Stillwaer, Minn.

[73] Assignee: Medtronic, Inc., Minneapolis, Minn.

[21] Appl. No.: 86,289

[22] Filed: Jul. 1, 1993

[51] Int. Cl.⁵ ............................................. A61N 1/05
[52] U.S. Cl. ........................................................ 607/127
[58] Field of Search ............... 128/642; 607/119, 122, 607/123, 125, 126, 127, 128, 131

[56] References Cited

U.S. PATENT DOCUMENTS

| | | | |
|---|---|---|---|
| 3,472,234 | 10/1969 | Tachick | 607/131 |
| 4,000,745 | 1/1977 | Goldberg | 607/127 |
| 4,010,758 | 3/1977 | Rockland . | |
| 4,106,512 | 8/1978 | Bisping . | |
| 4,628,943 | 12/1986 | Miller . | |
| 4,934,049 | 6/1990 | Keikhaffer . | |
| 4,951,687 | 8/1990 | Ufford . | |
| 5,044,375 | 9/1991 | Bach, Jr. . | |
| 5,050,601 | 9/1991 | Kupersmith . | |
| 5,115,818 | 5/1992 | Holleman . | |
| 5,143,089 | 9/1992 | Alt . | |
| 5,143,090 | 9/1992 | Dutcher et al. | 607/126 X |
| 5,144,960 | 9/1992 | Mehra . | |
| 5,217,028 | 6/1993 | Dutcher et al. | 128/642 X |

*Primary Examiner*—Lee S. Cohen
*Assistant Examiner*—Jeffrey R. Jastrzab
*Attorney, Agent, or Firm*—Reed A. Duthler; Harold R. Patton

[57] ABSTRACT

A defibrillation lead provided with an elongated defibrillation electrode and a bipolar electrode pair for cardiac pacing and sensing. The cardiac pacing and sensing electrodes comprise an extendable helical electrode and a ring or ring tip electrode located on or adjacent the distal end of the lead body. Inter-electrode separation for pacing and sensing is provided by means of insulation applied to the helical electrode, leaving only the tip portion exposed. The overall configuration of the lead allows the defibrillation electrode to be located very close to the distal end of the lead body, while preserving the ability to employ a bipolar electrode pair for cardiac pacing and sensing.

5 Claims, 1 Drawing Sheet

TRANSVENOUS DEFIBRILLATION LEAD

BACKGROUND OF THE INVENTION

The present invention relates to medical electrical leads generally and more particularly to implantable defibrillation electrodes and leads.

For some time, it has been recognized that in the context of implantable cardioverters and defibrillators, an electrode system employing transvenous leads alone or combination with subcutaneous electrodes provides substantial advantages as compared to epicardial electrode systems. In this context, use of a defibrillation electrode located in the right ventricle is conventional. In such leads, the defibrillation electrode typically takes the form of an elongated coil, mounted exterior to the insulative body of the lead.

In electrode systems presently under clinical evaluation, and presently for sale commercially outside the United States, right ventricular defibrillation leads typically also include one or more electrodes for cardiac pacing and sensing. It has been recognized for some time that the use of a bipolar electrode pair, mounted to such a right ventricular defibrillation lead is desirable. For example, U.S. Pat. No. 5,044,375 issued to Bach et al. discloses such a lead, as does U.S. Pat. No. 5,050,601 issued to Kupersmith and U.S. Pat. No. 5,144,960 issued to Mehra.

Like cardiac pacing leads, implantable defibrillation leads benefit from the inclusion of fixation apparatus. Passive fixation apparatus, such tines, are disclosed for example in the above cited Bach reference. Active fixation devices, such as metal helixes which are screwed into the heart tissue, are disclosed in the above-cited Kupersmith and Mehra et al. patents. In the right ventricular defibrillation leads presently manufactured and sold by Medtronic, two electrodes are provided for pacing and sensing, one taking the form of an advanceable helical electrode as generally disclosed in U.S. Pat. No. 4,106,512 issued to Bisping, the second electrode taking the form of a ring electrode. Both the helical electrode and the ring electrode are mounted distal to an elongated defibrillation electrode.

Generally, in order to accomplish reliable sensing of ventricular depolarizations employing a bipolar electrode pair, an intra-electrode spacing of 5 mm or more is generally believed desirable. In addition, some degree of spacing between the sensing electrodes and the right defibrillation electrode is also believed desirable. These constraints, taken together, have typically resulted in practical defibrillation lead designs in which the distal end of the defibrillation electrode is substantially spaced from the distal end of the lead body.

The present invention is directed towards optimizing the size, spacing and location of the electrodes on a defibrillation lead of the type including an elongated defibrillation electrode and two electrodes used for sensing of cardiac depolarizations. In particular, the invention is directed toward providing a bipolar sensing pair of electrodes having adequate interelectrode spacing to assure appropriate sensing of cardiac depolarizations, while still allowing placement of the defibrillation electrode as close to the distal end of the lead body as possible.

The present invention accomplishes these desired results by employing an electrode set comprising a helical electrode, extending distally from the lead body, for use as the active electrode in cardiac pacing and for use in sensing cardiac depolarizations. A ring tip electrode or a cylindrical ring electrode is located at or adjacent to the distal end of the lead body, and provides the second electrode for use in sensing depolarizations. The helical electrode is insulated from the point it exits the lead body until a point adjacent its distal end, thereby spacing the effective electrode surface of helical electrode about one-half centimeter or greater from the ring electrode. The defibrillation electrode is mounted with its distal end closely adjacent the distal end of the lead body as well, such that its distal end point is within one centimeter of the distal end of the lead body, which is made possible by the configuration of the ring and helical electrodes, as discussed above.

While the individual piece parts necessary to assemble the present invention may be found in individual prior art references, their combination, as discussed above, provides the synergistic result of a defibrillation lead having the distal end of its defibrillation electrode closely spaced to the end of the lead body, while retaining a bipolar electrode pair for sense which has adequate interelectrode separation.

BRIEF DESCRIPTION OF THE DRAWINGS

FIG. 1 illustrates a first embodiment of a lead according to the present invention.

Figure 1:
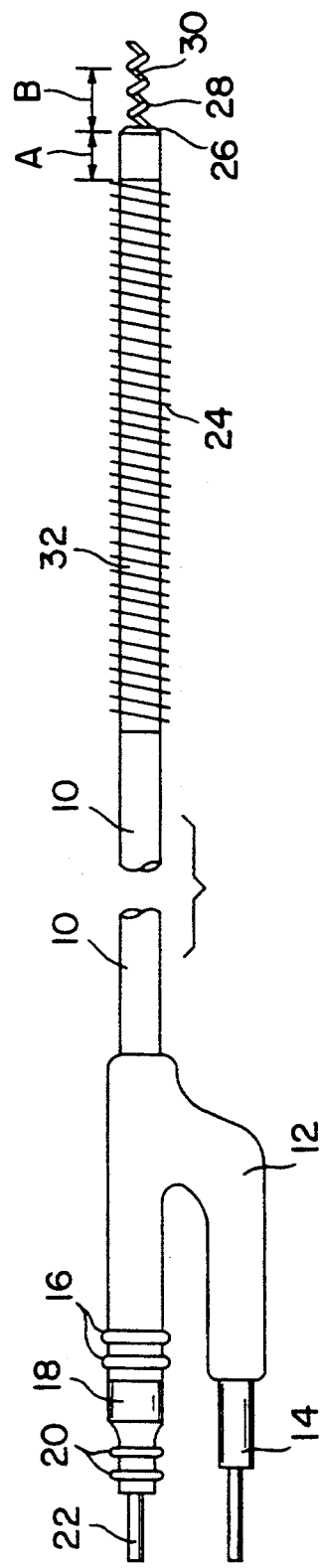
FIG. 1 is a plan view of a lead according to the present invention.

The lead is provided with an elongated outer insulation sheath 10, which enclosed three coaxial, arranged mutually insulated conductors. One of the conductors is coupled to the defibrillation electrode 24, which takes the form of an elongated coil of a biocompatible metal such as platinum or platinum alloy. A second one of the conductors is coupled to the ring electrode 26, which is located at the distal end of the lead body, and may similarly be fabricated of platinum, platinum alloy, stainless steel or other biocompatible metal. The third conductor is coupled to the helical electrode 28, which is extendable from the distal end of the lead body, by rotation of the third coiled conductor, as described in the above cited U.S. Pat. No. 4,106,512 issued to Bisping and incorporated herein by reference in its entirety. The majority of the length of electrode 28 is insulated, from the point it exits the lead body, up to a point 30, beyond which the electrode is uninsulated. As such, the distance between point 30 at which the helical electrode 28 is uninsulated and the ring electrode 26, illustrated as "B" defines the effective interelectrode spacing for purposes of sensing depolarizations. The distal end of electrode 24 is mounted a distance "A" from the distal end of the lead body, which distance is preferably one centimeter or less. An insulative backfill of silicone rubber or polyurethane 32, stabilizes the coil 24 around the outer insulative sheath 10.

The proximal end of the lead is provided with a connector assembly 12, which may correspond to any connector assembly according to the prior art having at least three connector surfaces. As illustrated, the connector assembly corresponds to those employed on transvenous ventricular defibrillation electrode leads of the type sold by Medtronic, Inc., and includes a stepped conductive pin 14, which is coupled to first coiled conductor, and thereby is coupled to defibrillation electrode 24. The connector assembly 12 also includes a connector ring 18, coupled to the second coiled conductor discussed above and thereby coupled to ring electrode 26 and a connector pin 22, coupled to the third coiled conductor discussed above, and thereby coupled to helical electrode 28. Pin 22 is rotatable, so that the third coiled conductor can be rotated to extend the helical electrode 28 as discussed in the above-cited Bisping patent. The connector assembly 12 is also provided with sealing rings 20 and 16 to provide fluid seals for connectors 22 and 18. U.S. Pat. No. 4,951,687 issued to Ufford et al., incorporated herein by reference in its entirety, illustrates an appropriate mechanism for providing a rotatable connector pin.

As implanted, ring electrode 26 will be located directly adjacent the tissue at the apex of the right ventricle, with the result that, as implanted, the distal end of electrode 24 is correspondingly spaced a centimeter or less from the apex of the right ventricle, providing for a defibrillation electrode location which is as close to the apex as practicable, while retaining an adequately spaced bipolar electrode pair for sensing of ventricular depolarizations.

Figure 2:
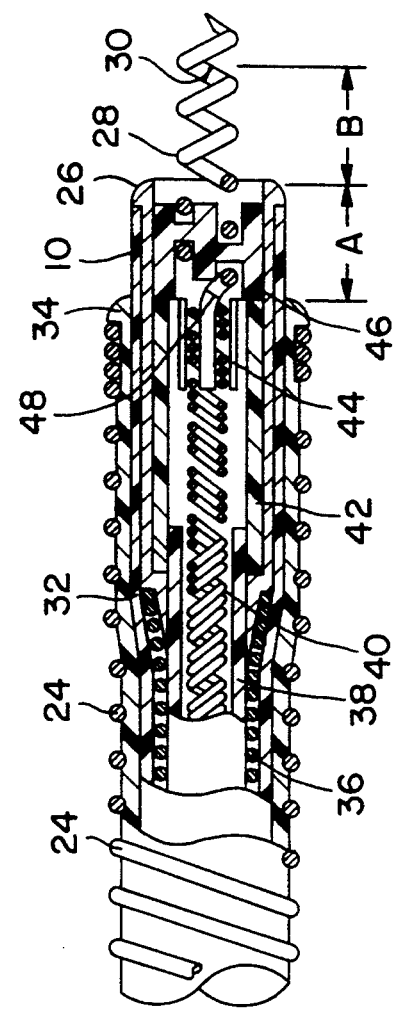
FIG. 2 is a cutaway view through the distal end of the lead illustrated in FIG. 1.

FIG. 2 is a cutaway view of the distal end of the lead illustrated in FIG. 1. In this view, the second coiled conductor 36 and third coiled conductor 40 are visible. The third coiled conductor 40 is coupled to the helical electrode 28 by means of a crimp sleeve 44, compressing electrode 28 between the coils of conductor 40. Helical electrode 28 passes through a guide member 46, which is arranged such that rotation of helical electrode 28 causes its advancement out of the distal end of the lead body. As illustrated, coiled electrode 28 is insulated from a point 48, within the lead body, up to a point 30, which is located distal to the end of the lead body, when the electrode 28 is fully extended.

Ring electrode 26 extends proximally within the lead body to define a rigid electrode head. Second coiled conductor 36 is welded to the proximal end of ring electrode 26, in order to electrically and mechanically couple the conductor to the electrode. Located within the body of electrode 26 is an inner insulative sleeve 42, which insulates third conductor 40 from the interior surface of the body of ring electrode 26. The exterior surface of the body of ring electrode 26 is covered by outer insulative sheath 10, up to a point adjacent the distal end of the lead.

Mounted externally to outer sheath 10 is the defibrillation electrode 24, which is terminated distally at a circular sleeve 34, to which it is welded. Backfill 32 is visible between the individual turns of coil electrode 24, and may be provided according to the methods disclosed in U.S. Pat. No. 4,934,049 issued to Kiekhaffer or U.S. Pat. No. 5,115,818 issued to Holleman et al., both of which are incorporated herein by reference in their entireties. Backfill 32 may be provided by filling between the coils using silicone rubber adhesive or by expanding an internal tubular sleeve against the coils while heated.

As illustrated in FIG. 2, the effective electrode surface of electrode 26 is located at the most distal extremity of the lead body, with all inter-electrode spacing provided by the insulation on helical electrode 28. In some embodiments, it may be desired to accomplish a greater degree of interelectrode spacing or employ a shorter helix, and thus in some embodiments, it may be desirable to move the effective electrode area of ring electrode 26 slightly proximally (e.g., a few millimeters) along the lead body, which may readily be accomplished without requiring the proximal displacement of the defibrillation electrode 24. Similarly, while the present invention is illustrated employing a helical electrode which is advanceable from within the electrode head, the invention may also be practiced by use of a fixed helical electrode, which would substantially simplify the overall structure distal end of the lead, and would permit reduction in overall outer diameter, which may be desirable in some circumstances. In such case, counter rotation of the lead, as presently practiced in conjunction with fixed screw endocardial pacing leads, would be practiced as part of the implantation technique.

While the above embodiment discloses the use of electrodes which are fabricated of conductive biocompatible metals, there has been recent work toward development of defibrillation electrode systems employing electrodes of carbon fiber or other conductive material. For example, see U.S. Pat. No. 5,143,089, issued to Alt, incorporated by herein by reference in its entirety. The present invention is believed useful in conjunction with leads employing defibrillation electrodes of such alternate materials and configurations as well, and should not be construed as limited to electrodes fabricated using the presently conventional form of a helical coil of biocompatible metal. The same considerations hold true with regard to the materials disclosed herein for conductors and insulators, which are provided purely as examples of appropriate materials.

The above specification should thus be read as exemplary, rather than limiting, with regard to the scope of the claims which follow. In conjunction with the above specification I claim:

1. An implantable defibrillation lead, comprising:
    an elongated lead body having a proximal end and a distal end;
    first, second and third mutually insulated conductors located within said lead body;
    first, second and third electrical connectors, each coupled to one of said first, second and third mutually insulated conductors;
    an elongated defibrillation electrode having proximal and a distal end, mounted to said lead body such that the distal end of said defibrillation electrode is located about one centimeter or less from the distal end of said lead body; and
    first and second sensing electrodes, mounted to said lead body, distal to the distal end of said defibrillation electrode; and having an interelectrode spacing of about 0.5 centimeter;
    wherein said first sensing electrode comprises a helical electrode extending from the distal end of said lead body, said helical electrode provided with an insulative coating extending to a point distal to the distal end of said lead body, and wherein said second sensing electrode comprises an electrode mounted to the distal end of said lead body, distal to the distal end of said defibrillation electrode.

2. A lead according to claim 1 wherein said helical electrode is provided with an insulative coating extending to a point about one-half centimeter or greater from said second sensing electrode.

3. A transvenous defibrillation lead, comprising:
    an elongated lead body;
    first, second and third mutually insulated conductors located within said elongated lead body;

first, second and third electrical connectors mounted to said lead body, each coupled to one of said first, second and third mutually insulated conductors;

an elongated defibrillation electrode having a proximal end and a distal end and coupled to said first conductor, said distal end of said defibrillation electrode located adjacent the distal end of said lead body;

a first sensing electrode, coupled to said second conductor and located adjacent the distal end of said lead body, distal to the distal end of said defibrillation electrode; and a helical electrode, coupled to said third conductor and extending from the distal end of said lead body, said helical electrode provided with an insulative coating extending to a point about 0.5 centimeters or greater from said first sensing electrode.

4. A lead according to claim 3 wherein said first sensing electrode is located at the distal end of said lead body.

5. A transvenous defibrillation lead, comprising:

an elongated lead body having proximal and distal ends;

first, second and third mutually insulated conductors located within said elongated lead body;

first, second and third electrical connectors mounted to said lead body, each coupled to one of said first, second and third mutually insulated conductors;

an elongated defibrillation electrode having a proximal end and a distal end and coupled to said first conductor, said distal end of said defibrillation electrode located within about 1 centimeter of the distal end of said lead body;

a first sensing electrode, coupled to said second conductor and located at the distal end of said lead body; and a helical electrode, coupled to said third conductor and extending from the distal end of said lead body, said helical electrode provided with an insulative coating extending to a point distal to the distal end of said lead body.

* * * * *